(12) United States Patent
Webler

(10) Patent No.: US 8,521,262 B2
(45) Date of Patent: Aug. 27, 2013

(54) METHODS AND APPARATUS FOR LOCALIZATION, DIAGNOSIS, CONTACT OR ACTIVITY DETECTION OF BIO-ELECTRIC TISSUE

(75) Inventor: William E. Webler, Escondido, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 608 days.

(21) Appl. No.: 12/482,255

(22) Filed: Jun. 10, 2009

(65) Prior Publication Data

US 2009/0240163 A1 Sep. 24, 2009

Related U.S. Application Data

(62) Division of application No. 11/486,828, filed on Jul. 13, 2006, now abandoned.

(51) Int. Cl.
*A61B 5/0402* (2006.01)
*A61B 5/04* (2006.01)

(52) U.S. Cl.
USPC .......................................... 600/509; 600/508

(58) Field of Classification Search
USPC .................................. 600/508–522
See application file for complete search history.

(56) References Cited

U.S. PATENT DOCUMENTS

| | | | |
|---|---|---|---|
| 4,321,932 A | | 3/1982 | Francis |
| 5,133,349 A * | | 7/1992 | Heinze .............................. 607/22 |
| 5,431,649 A * | | 7/1995 | Mulier et al. .................... 606/41 |
| 5,447,529 A * | | 9/1995 | Marchlinski et al. ........... 607/99 |
| 5,921,939 A * | | 7/1999 | Danielsson et al. ........... 600/509 |
| 6,004,269 A | | 12/1999 | Crowley et al. |
| 6,052,617 A | | 4/2000 | Kim |
| 6,052,618 A | | 4/2000 | Dahlke et al. |
| 6,144,881 A | | 11/2000 | Hemming et al. |
| 6,163,724 A | | 12/2000 | Hemming et al. |
| 6,205,357 B1 | | 3/2001 | Ideker et al. |
| 6,236,882 B1 | | 5/2001 | Lee et al. |
| 6,496,721 B1 * | | 12/2002 | Yonce ........................... 600/509 |
| 6,597,942 B1 * | | 7/2003 | Yonce ........................... 600/509 |

(Continued)

FOREIGN PATENT DOCUMENTS

EP  0614678  9/1994

OTHER PUBLICATIONS

"International Search Report and Written Opinion of the International Searching Authority Dated Nov. 5, 2007", International Application No. PCT/US2007/013275.

(Continued)

*Primary Examiner* — Allen Porter, Jr.
(74) *Attorney, Agent, or Firm* — Blakely, Sokoloff, Taylor & Zafman LLP

(57) ABSTRACT

Methods and apparatus for localization, diagnosis, contact or activity detection of bio-electric tissue providing improved sensitivity to the distance between a sensing electrode and bio-electric tissue and providing the means to measure the impedance of the tissue between a sensing electrode and bio-electric tissue. In accordance with the method, a controlled effective input impedance is provided to the monitor, which input impedance can be set to cause a significant portion of the bio-electric tissue signal to be dropped across the tissue between a sensing electrode and the bio-electric tissue when the two are separated by a predetermined or arbitrary distance. Various illustrative embodiments and forms of construction are disclosed.

17 Claims, 3 Drawing Sheets

(56) References Cited

U.S. PATENT DOCUMENTS

| | | |
|---|---|---|
| 6,615,073 B1 * | 9/2003 | Panescu et al. .............. 600/509 |
| 6,745,074 B1 | 6/2004 | Obel |
| 6,807,438 B1 | 10/2004 | Brun Del Re et al. |
| 6,839,587 B2 * | 1/2005 | Yonce .......................... 600/509 |
| 6,850,800 B1 | 2/2005 | Uhrenius et al. |
| 6,909,919 B2 | 6/2005 | Jain et al. |
| 6,950,694 B2 * | 9/2005 | Yonce .......................... 600/509 |
| 2002/0128689 A1 | 9/2002 | Connelly et al. |
| 2002/0138012 A1 * | 9/2002 | Hodges et al. ................ 600/509 |
| 2002/0183635 A1 | 12/2002 | Yonce |
| 2002/0183738 A1 * | 12/2002 | Chee et al. ..................... 606/41 |
| 2003/0060866 A1 | 3/2003 | Schmidt |
| 2003/0073916 A1 | 4/2003 | Yonce |
| 2004/0010291 A1 * | 1/2004 | Wagner et al. .................. 607/5 |
| 2004/0049238 A1 | 3/2004 | Jarverud |
| 2004/0054383 A1 | 3/2004 | Ryan et al. |
| 2004/0064059 A1 | 4/2004 | Samuelson et al. |
| 2004/0077961 A1 | 4/2004 | Yonce |
| 2004/0133113 A1 * | 7/2004 | Krishnan ..................... 600/508 |
| 2004/0158290 A1 | 8/2004 | Girouard et al. |
| 2004/0167580 A1 | 8/2004 | Mann et al. |
| 2004/0172080 A1 | 9/2004 | Stadler et al. |
| 2004/0199082 A1 | 10/2004 | Ostroff et al. |
| 2004/0215271 A1 | 10/2004 | Sullivan |
| 2005/0038350 A1 | 2/2005 | Kamath et al. |
| 2005/0102001 A1 | 5/2005 | Maile et al. |
| 2005/0131478 A1 | 6/2005 | Kim et al. |

OTHER PUBLICATIONS

Cassidy, Dennis M., et al., "The value of catheter mapping during sinus rhythm to localize site of origin of ventricular tachycardia", *Circulation, Journal of the Heart Association*, vol. 69, No. 6, (Jun. 1984), pp. 1103-1110.

Cinca, Juan, et al., "Passive transmission of ischemic ST segment changes in low electrical resistance myocardial infarct scar in the pig", *Cardiovascular Research*, No. 40, (1998), pp. 103-112.

Fallert, Michael A., et al., "Myocardial Electrical Impedance Mapping of Ischemic Sheep Hearts and Healing Aneurysms", *Circulation, Journal of the American Heart Association*, vol 87, No. 1, (Jan. 1993), pp. 199-207.

Schwartzman, David, et al., "Electrical Impedance Properties of Normal and Chronically Infarcted Left Ventricular Myocardium", *Journal of Interventional Cardiac Electrophysiology*, No. 3, (1999), pp. 213-224.

* cited by examiner

METHODS AND APPARATUS FOR LOCALIZATION, DIAGNOSIS, CONTACT OR ACTIVITY DETECTION OF BIO-ELECTRIC TISSUE

CROSS-REFERENCE TO RELATED APPLICATION

This application is a divisional of U.S. patent application Ser. No. 11/486,828 filed Jul. 13, 2006.

BACKGROUND OF THE INVENTION

1. Field of the Invention

The present invention relates to the field of detecting bio-electric activity of tissue.

2. Prior Art

Using modern ECG monitors to determine, for instance, when an electrode is in contact with live contractile heart tissue, to differentiate live from dead contractile heart tissue or to localize Purkinje fibers is difficult using modern ECG monitors because there is little difference in displayed signal amplitudes between when an electrode is very near, nearing, moving further away from, in contact with or a few centimeters away from an electrically active tissue.

The reason for this lack of significant change in signal amplitudes is the high input impedance of modern ECG and other bio-electrical activity monitors. For instance, an input impedance/resistance of $10^{12}$ ohms is not unusual for an input amplifier of a monitor. Of course, for monitoring purposes, this high input impedance is desirable, as the signal levels are thus as high and as constant as possible, allowing standardized monitoring procedures and diagnosis despite variations in sensing electrode placement or electrode impedance. Also, the gain range in the monitors may be smaller and gain adjustment is often not necessary to obtain a well-defined signal. From a historical perspective, the development of higher input impedance amplifiers also improved patient safety by reducing leakage currents and the like.

DETAILED DESCRIPTION OF THE PREFERRED EMBODIMENTS

Figure 1:
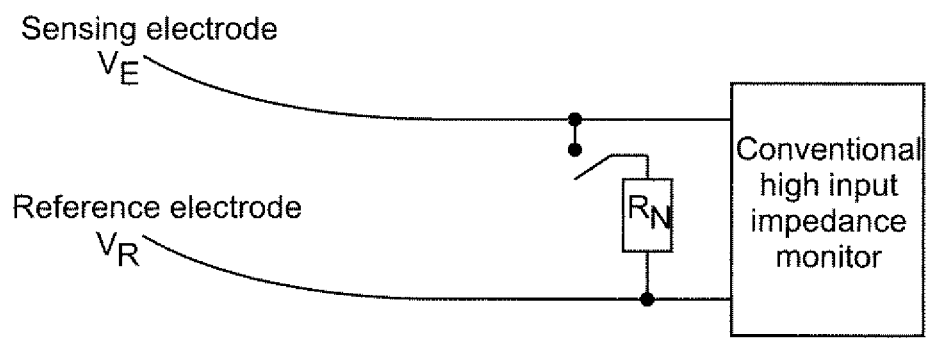
FIG. 1 is a schematic representation of one embodiment of the present invention using a selectable predetermined input impedance to a monitor.

The preferred embodiments of the present invention provide a monitoring circuit with a reduced input impedance to cause more current to flow in the sensing circuit, and thus cause more of a signal drop across the resistance of the intervening tissue (like blood, heart tissue, muscle tissue, skin, etc.) between the sensing electrode and the electrically active tissue to be localized or sensed. The voltage drop is in an amount responsive to the distance between the sensing electrode and the electrically active tissue. This may be achieved, by way of example, by using a typical sensing circuit and adding a suitable resistance across the sensing and reference electrodes or the electrode connections to an otherwise high input impedance monitor to raise the signal current in the sensing circuit and thus, drop more of the signal voltage across the tissue between the sensing electrode and the electrically active tissue. Thus, the closer the sensing electrode gets to the tissue, the lower the resistance of the intervening tissue becomes, and the less of the signal is dropped across the intervening tissue. With less signal dropped, the amplitude of the signal sensed by the monitor increases. Thus, as the sensing electrode is moved toward the tissue producing the electrical signal of interest, the signal sensed by the monitor increases significantly and, conversely, as the sensing electrode is moved further away from the tissue producing the electrical signal of interest, the signal sensed by the monitor decreases significantly. (In conventional monitors, the input impedance of the monitor is so high that there is very little current in the sensing circuit, so there is very little signal dropped across the resistance of the intervening tissue and thus, there is very little change in the monitored signal amplitude as the distance to the electrically active tissue is changed.)

The resistor effectively lowering the input impedance of the monitor may be mounted in the device/catheter with the sensing and reference electrode(s) or in the input of the monitor, thereby allowing the use of a conventional monitor. A switch(s) or switching device(s) may also be incorporated to allow the resistor(s) to be switched into and/or out of the circuit(s) to allow the electrodes to be used for the normal monitoring or other purposes, as well as for localization purposes. Because the resistor(s) and/or switches need not be connected to an active power supply, they may be passive devices. Alternatively the switch(s) may be constructed from modern active switching devices, while still maintaining patient safety.

Because the voltage of the electrical signals generated by the heart and nervous tissue are very close to the same from one individual to another individual, the variations in tissue (like blood) bulk resistance are limited from one individual to the another individual, and practical sensing electrode distances from the electrically active tissue within or across the anatomy are limited from one individual to the another individual, one might choose to use a fixed or standard input impedance(s) that will provide standardized signal level changes or indications to aid in the localization or diagnosis of bio-electrically active tissue(s). Such an arrangement can have the advantages of providing a standard localization "feel" for the device and/or standard diagnosis signal level change and/or indication change values.

Figure 2:
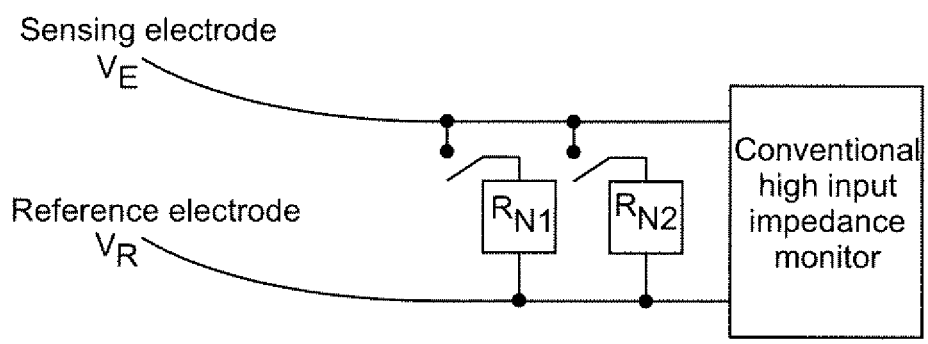
FIG. 2 is a schematic representation of one embodiment of the present invention using a selection of multiple predetermined input impedances to a monitor.
Figure 3:
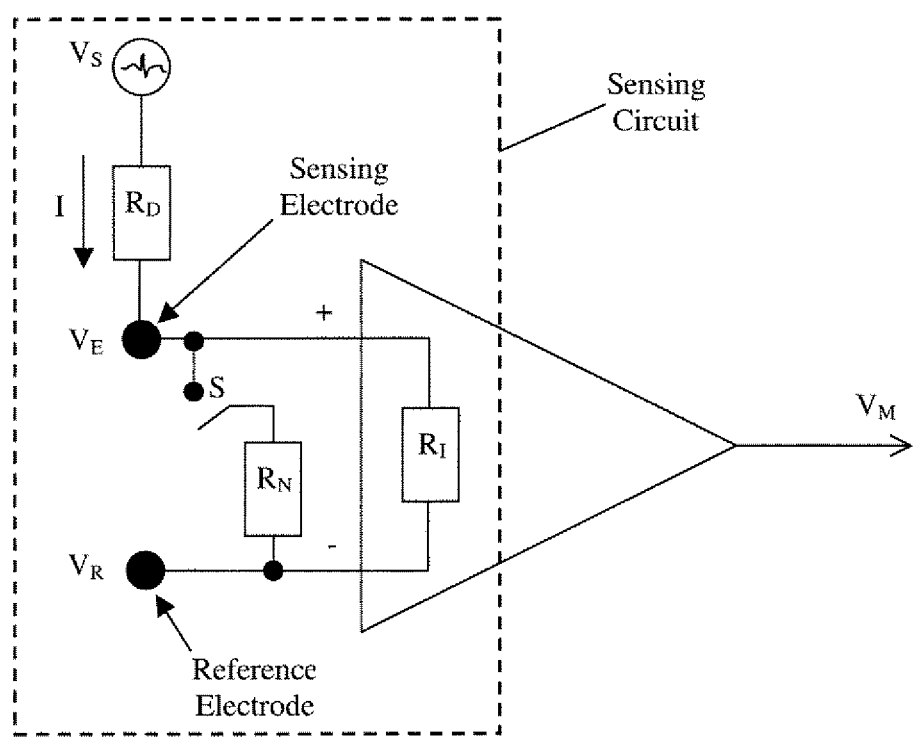
FIG. 3 is a simplified circuit diagram for the input circuit to a monitor for certain embodiments of the present invention.

Now referring to FIGS. 1, 2 and 3, two schematic block diagrams and a simplified circuit diagram of an electrode pair and monitor or monitor input circuit may be seen. The sensing electrode for sensing the bio-electric signal $V_S$ may be of a conventional monitoring electrode design or a special electrode design fabricated for this specific purpose. The reference electrode design may also be a conventional reference electrode design, if desired, a single electrode or a composite of several electrodes, as is well known in the art of ECG monitoring. It is preferred that the reference electrode be in contact with the body tissue at a greater distance from the bio-electric tissue of interest than the sensing electrode. It is also preferred that the reference electrode's position be constant or experience less motion (less percent change in distance relative to the tissue generating the bio-electric signal of interest) than the sensing electrode. As shown in FIG. 1, the monitor may be a conventional high input impedance ECG monitor with a resistor external to the monitor being switchable across a pair(s) of the monitor input terminals to effectively controllably reduce the apparent input impedance of the monitor as seen by the sensing circuit to a predetermined value, or at least a predetermined value for the specific application of the invention. In that regard, FIG. 2 is a similar block diagram illustrating the use of multiple, different valued resistors that may be switched into the circuit individually or in combination to provide a choice of input impedances. In other embodiments, an adjustable or variable resistor may be used. In any event, FIG. 3 illustrates a simplified or lumped equivalent circuit for the electrodes and the input amplifier of the monitor, where $R_I$ represents the normally very high input impedance of the monitor input amplifier and $R_N$ represents the resistance of the new resistor or variable/adjustable resistor or the combined resistance of the new resistors switchably coupled across the monitor input and/or across the electrode leads. $R_D$ represents the resistance between the tip of the sensing electrode and the bio-electric tissue being sensed (plus any resistance associated with the reference electrode or the electrode leads, which can be designed to be negligible and/or a relatively constant/known value using methods known to the art). $V_S$ represents the bio-electric tissue signal voltage of interest and $V_E$ represents the portion of the bio-electric tissue signal voltage $V_S$ applied to one side of the monitor input via the sensing electrode. $V_R$ represents the reference voltage or voltage signal applied to the other side of the monitor input via the reference electrode. $V_M$ represents the output or response of the monitor's input amplifier. It can be shown that a greater monitor response (change in $V_M$) to a variation in proximity of the tip of the sensing electrode to the bio-electric tissue occurs when switch S is closed and the resistance of the combination of resistors $R_I$ and $R_N$ is chosen, for example, such that it equals the resistance $R_D$ of the intervening tissue at some distance from the tissue, or:

$$R_D = \frac{1}{\frac{1}{R_I} + \frac{1}{R_N}}$$

Using this value, the current I through the sensing circuit is:

$$I = \frac{V_S - V_R}{R_D + \frac{1}{\frac{1}{R_I} + \frac{1}{R_N}}} = \frac{V_S - V_R}{R_D + R_D} = \frac{V_S - V_R}{2R_D}$$

Assuming the monitor input amplifier has a gain of one (for convenience, the monitor input amplifier is assumed to have gain of one throughout all of the following descriptions), the voltage level sensed or displayed by the monitor is then:

$$V_M = \frac{R_D(V_S - V_R)}{2R_D} = \frac{(V_S - V_R)}{2}$$

Thus, if $R_N$ is chosen so that:

$$R_D = \frac{1}{\frac{1}{R_I} + \frac{1}{R_N}}$$

when the tip of the sensing electrode is at a distance of say 1 cm from the bio-electric tissue signal source $V_S$, then the monitor will sense one half the full voltage difference generated between the bio-electric tissue $V_S$ and the reference $V_R$. If the sensing electrode is now moved closer to the bio-electric tissue such that resistance of the tissue $R_D$ becomes ½ its former value, then the new current I' through the sensing circuit becomes:

$$I' = \frac{V_S - V_R}{R_D/2 + R_D} = \frac{2(V_S - V_R)}{3R_D}$$

Thus, the new voltage $V_M'$ sensed or displayed by the monitor becomes:

$$V_M' = \frac{2R_D(V_S - V_R)}{3R_D} = \frac{2(V_S - V_R)}{3}$$

Thus, the change in voltage sensed or displayed by the monitor as a result of this sensing electrode motion toward the bio-electric tissue is:

$$V_M' - V_M = \frac{2(V_S - V_r)}{3} - \frac{(V_S - V_r)}{2} = \frac{(V_S - V_r)}{6}$$

This is to be compared with a prior art high input impedance monitor where $R_I$ is much larger than $R_D$ for reference and sensing electrodes on or within the body. Under these conditions, the values of $R_D$ are very much lower than $R_I$, so substantially the full voltage generated by the bio-electric tissue relative to the reference ($V_S - V_R$) is sensed by the monitor in either sensing electrode position, and there is very little variation in the voltage sensed or displayed with sensing electrode position changes relative to the bio-electric tissue.

Illustrating this lack of change in mathematical terms, without $R_N$ in the sensing circuit (switch S open, as shown in FIG. 3), the current I in the sensing circuit is:

$$I = \frac{V_S - V_R}{R_D + R_I}$$

Thus, the voltage $V_M$ sensed or displayed by the monitor becomes:

$$V_M = \frac{R_I(V_S - V_R)}{R_D + R_I}$$

However, because $R_I$ is so much larger than $R_D$, for practical purposes:

$$\frac{R_I}{R_D + R_I} \approx 1$$

Note that a typical value of $R_D$ may be on the order of $10^4$ ohms or considerably less (as determined using catheter mounted intraventricular sensing electrodes and sensing needle electrodes in animal experiments with the catheter mounted reference electrode located in the Aorta) and a typical value of $R_I$ may be on the order of $10^{12}$ ohms (from technical data sheets of amplifiers with JFET input stages).

Therefore, for practical purposes, the voltage $V_M$ sensed or displayed by the monitor becomes, regardless of sensing electrode position changes (changes in $R_D$):

$$V_M \approx V_S - V_R$$

Thus, the invention is used to provide greater changes in the sensed or displayed bio-electric signal levels as a sensing electrode is moved through tissue (blood is a tissue) closer to or away from a bio-electric tissue of interest. For an IV (intraventricular) catheter, this can be used in several ways. One way is to determine when the tip of a sensing electrode is in contact with living heart muscle tissue. As the tip of the sensing electrode is moved toward the heart muscle through the blood in the LV (left ventricle), the monitored ECG signal level (Q-R-S-T segment related to ventricular electrical activity) sensed by the tip of the sensing electrode will increase and peak when it contacts the heart tissue. Also, when the sensing electrode contacts the heart tissue there will be little or no difference between the voltage sensed or displayed by the monitor between when a well-chosen $R_N$ is switched into the sensing circuit and when $R_N$ is switched out of the sensing circuit.

Another application is to aid in the diagnosis of heart tissue. If the heart tissue is scar tissue, dead tissue or other not bio-electrically active tissue, then the changes in the ECG amplitude will be much less as the tip of the sensing electrode is brought into contact with the tissue than when approaching a bio-electrically active tissue. Also, when the sensing electrode contacts bio-electrically active heart tissue, there will not be a significant difference between the voltage sensed or displayed by the monitor between when a well-chosen $R_N$ is switched into the sensing circuit and when $R_N$ is switched out of the sensing circuit. However, when the sensing electrode contacts heart tissue that is scar tissue, dead tissue or other not bio-electrically active tissue, there will be a significant difference between the voltage sensed or displayed by the monitor between when a well-chosen $R_N$ is switched into the sensing circuit and when $R_N$ is switched out of the sensing circuit.

When this information is combined with tissue motion/strain information, such as from a fluoroscope, sonogram or other imaging or detection system (e.g. CT imaging, a tip location system, a tip acceleration system), a tissue diagnosis may be made. Tissue with a large ECG signal increase when approached by a sensing electrode or (when the sensing electrode is in contact with the tissue) without a significant difference between the voltage sensed or displayed by the monitor between when a well-chosen $R_N$ is switched into the sensing circuit and when $R_N$ is switched out of the sensing circuit and high levels of motion is healthy tissue. Tissue with a large ECG signal increase when approached by a sensing electrode or (when the sensing electrode is in contact with the tissue) without a significant difference between the voltage sensed or displayed by the monitor between when a well-chosen $R_N$ is switched into the sensing circuit and when $R_N$ is switched out of the sensing circuit and low levels of motion is stunned tissue. Tissue with a small ECG signal increase when approached by a sensing electrode or (when the sensing electrode is in contact with the tissue) a significant difference between the voltage sensed or displayed by the monitor between when a well-chosen $R_N$ is switched into the sensing circuit and when $R_N$ is switched out of the sensing circuit and low levels of motion is dead or scar tissue.

Another, more complex, embodiment of this invention is to use it to measure/estimate $R_D$ using some form of the following simplified derivation:

With switch S open, $R_N$ not in the sensing circuit, as previously derived, for practical purposes:

$$V_M \approx V_S - V_R$$

With switch S closed, current in the sensing circuit I, is:

$$I = \frac{V_S - V_R}{R_D + \dfrac{1}{\dfrac{1}{R_N} + \dfrac{1}{R_I}}}$$

However, with $R_I$ very much larger than $R_N$, for practical purposes:

$$\frac{1}{\dfrac{1}{R_N} + \dfrac{1}{R_I}} \approx R_N$$

Therefore, the equation for 1 may be simplified to become:

$$I \approx \frac{V_S - V_R}{R_D + R_N}$$

Therefore, the new voltage sensed or displayed $V_M'$ becomes:

$$V_M' \approx \frac{R_N(V_S - V_R)}{R_D + R_N}$$

Substituting $V_M$ for $V_S - V_R$ and solving for $R_D$:

$$R_D \approx \frac{R_N(V_M - V_M')}{V_M'}$$

Thus, the resistance of the tissue between the sensing electrode (plus other reference and sensing electrode associated resistances) and the bio-electric tissue may be easily determined/estimated from known ($R_N$) and measured parameters ($V_M$ and $V_M'$). In some embodiments, such as where $R_N$ is standardized or constant, a parameter responsive to $R_D$ may be calculated and displayed or scaled to, for example, $$\frac{(V_M - V_M')}{V_M'}, \frac{V_M}{V_M'} - 1, \frac{V_M}{V_M'}$$

or, such as where, additionally, the bio-electric signal amplitudes ($V_S$) are relatively fixed, to, for example, $V_M - V_M'$ for simplicity.

Figure 4:
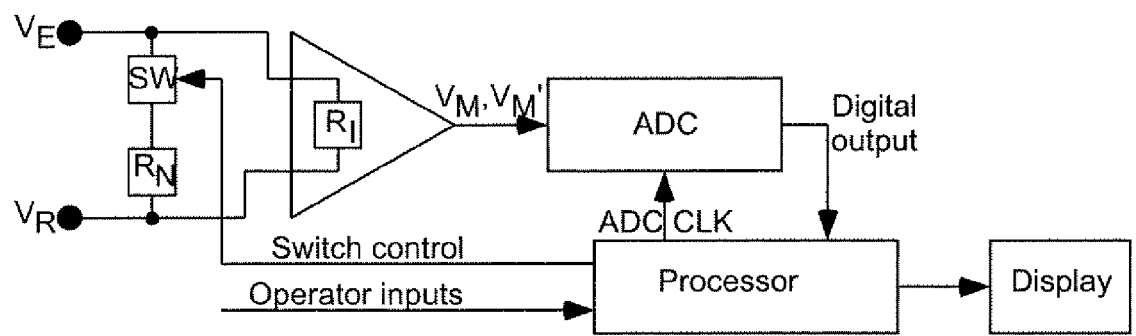
FIG. 4 is a block diagram of a processor controlled interface for certain embodiments of the present invention.

Because bio-electric tissue signals are much lower in frequency than the frequency responses of amplifier/input amplifier technology and electronic switching circuitry (as well as some part-mechanical switching components like mercury wetted relays), $R_N$ may be rapidly switched into and out of the sensing circuit to provide a rapidly updated calculated value of $R_D$ from the resulting adjacent values of $V_M$ and $V_M'$. For instance, as shown in FIG. 4, $V_M$ and $V_M'$ may be sampled using a switch SW and an analog to digital converter ADC, and the value of $R_D$ or a parameter responsive to the value of $R_D$ computed by a Processor and displayed in some manner, such as graphical or numerical. In other embodiments, the value of $R_N$ and/or the gain of the amplifier may also be under processor control and thus, for instance, the values of $V_M$, $V_M'$ and/or $V_M$-$V_M'$ controlled to provide optimum use of the voltage range and/or discrimination of the ADC. A display relating the timing of $R_D$ values to the timing of the sensed bio-electric signal waveform (from the sensing and reference electrodes without $R_N$ in the circuit) is preferred so that both may be displayed simultaneously and thus, the values of $R_D$ be more readily related to the tissue signal of interest. In a less preferred sampling embodiment, because the waveforms of bio-electric tissue signals are often very repeatable in shape or have portions that are very repeatable in shape, $V_M$ (or $V_M'$) may be sampled from the real-time bio-electric tissue signal and $V_M'$ (or $V_M$) sampled from the previously recorded bio-electric tissue signal waveform at or near the portion of the waveform analogous to the current portion of the real-time signal to provide a rapidly updated calculated value of $R_D$.

A rapidly updated calculated and displayed value(s) of $R_D$ can provide a quasi real-time indication of a sensing electrode's motion direction relative to a bio-electric tissue of interest. The preferred method of generating a rapidly updated $R_D$ display is especially useful in the case of ECG waveforms, which have a relatively long period and can change shape as the position of the sensing electrode (and/or reference electrode) is changed. If the value of $R_D$ is increasing for the bio-electric signal portion of interest, then the sensing electrode is moving away from the tissue of interest and, conversely, if the value of $R_D$ is decreasing for the bio-electric signal portion of interest, then the sensing electrode is moving toward the tissue of interest.

As one skilled in the art will recognize, $R_I$ is also a known/measurable parameter and may be included in derivations similar to the previous derivations to provide slightly more precise results. As is also well known in the art, rather than just resistances, impedance values (including frequency dependent reactance(s), as well as resistance) may be used with similar mathematic relationships (and/or as a replacement for $R_N$) as in the previous derivations. Such more complex mathematics also demonstrates the means to obtain greater changes in sensed or displayed signal levels with changes in the position of the sensing electrode relative to the bio-electric tissue and/or provides the means to estimate/calculate $R_D$ and/or its analogous impedance value. Another application is to aid in the localization of Purkinje fibers. The closer the sensing electrode (could be a needle tip electrode) approaches a Purkinje fiber, the larger will be its electrical signal spike prior to the "R" wave in the ECG and the lower will be the $R_D$ calculated for the signal spike. Another way is to compare the number of fibers in a Purkinje fiber bundle. Once the peak electrical signal spike (or minimum spike $R_D$) is obtained by a needle sensing electrode (penetrating a wall of the heart), the relative amplitudes of the peaks obtained with the same well chosen $R_N$ switched into the sensing circuit will indicate the relative size of the fiber bundles—the higher the peak amplitude, the more fibers in the bundle. This occurs because of the inherent resistance of each fiber. With more than one fiber, these individual resistances are effectively in parallel and thus, drop less voltage. The more fibers, the less voltage dropped across the fiber resistance. For this reason, the minimum $R_D$ of a fiber bundle with more fibers will be smaller than the minimum $R_D$ of a fiber bundle with less fibers.

A product in accordance with the present invention could include all electrodes, resistances, switches and the monitor. However as previously noted, a conventional sensing and reference electrode may be used as well as a conventional monitor. Thus the invention may be practiced by providing an interface to go between a sensing and reference electrodes and a monitor with the interface containing the appropriate switch(es)/resistance(s) for the purpose. Alternatively, such an interface may provide one or both of the sensing electrode and reference electrodes. Such interfaces may also include a connection to the monitor, by which the monitor may control the position(s) of the switch(es). Such an assembly or interface could be made disposable or reusable. In that regard, since the input impedance $R_I$ of prior art monitors is quite high compared to the tissue resistance $R_D$, variations in input impedance between different monitors or different manufacturers' monitors will have negligible effect on the operation of the present invention. A manual switch might be stable in either the on ($R_N$ in the sensing circuit) or off position ($R_N$ not in the sensing circuit), or alternatively, may be a spring return pushbutton switch for actuation when the electrode is being actively manipulated, but automatically returning to the off position for normal ECG monitoring when not being actively manipulated.

In another embodiment, a product in accordance with the present invention could be built into the proximal hub of a catheter. The catheter and/or its associated components may contain electrodes that may serve as sensing and/or reference electrodes and a proximal hub(s) of the catheter may contain the switch(es) and resistor(s) and electrode connections compatible with a conventional monitor. In some embodiments, a connection to the monitor, by which the monitor may control the position(s) of the switch(es), may be provided.

In another embodiment, a product in accordance with the present invention could be built into the monitor and be designed to be compatible with conventional electrodes, needle electrodes, catheter mounted electrodes, pacing electrodes and others.

In some embodiments, the monitor may be a part of a more complex system, such as a medical imaging machine, catheter position determining system or an implanted device.

The invention may be used to provide greater changes in sensed or displayed bio-electric signal levels as a sensing electrode moves through tissue (blood is a tissue) closer to or away from a bio-electric tissue of interest or to determine tissue resistance values using conventional ECG or nerve impulse monitors or conventional ECG or nerve impulse monitor technology modified in accordance with this invention. Standardized settings may be determined to aid in the localization or diagnosis of tissue based on bio-electric signal levels level changes, calculated tissue resistance and/or calculated tissue resistance changes.

Thus, while certain preferred embodiments of the present invention have been disclosed and described herein for purposes of illustration and not for purposes of limitation, it will be understood by those skilled in the art that various changes in form and detail may be made therein without departing from the spirit and scope of the invention.

The invention claimed is:

1. A method of determining bio-electric activity of normally bio-electric tissue comprising:
   causing a sensing electrode to touch a normally bio-electric cardiovascular tissue;
   measuring, using a monitor with a predetermined input impedance $R_1$, a response voltage $V_M'$ with a second predetermined impedance $R_N$ coupled between the sensing electrode and a reference electrode, and measuring a response voltage $V_M$ with the second predetermined impedance $R_N$ not coupled between the sensing electrode and the reference electrode, the response voltages $V_M'$ a and $V_M$ being the voltages generated in response to the normally bio-electric cardiovascular tissue being touched by the sensing electrode; and determining, by a processor, whether the normally bio-electric cardiovascular tissue is bio-electrically active or inactive, wherein determining is based on the measured values of $V_M$ and $V_M'$.

2. The method of claim 1 wherein determining whether the normally bio-electric cardiovascular tissue is bio-electrically active or inactive comprises comparing the measured value of $V_M'$ with a predetermined expected value of $V_M'$.

3. The method of claim 1 wherein determining the bio-electric activity of the normally bio-electric cardiovascular tissue comprises comparing a difference in the measured values of $V_M$ and $V_M'$ with a predetermined value of the difference.

4. The method of claim 1, further comprising:
calculating a parameter responsive to an impedance $R_D$ of the cardiovascular tissue between the sensing electrode and a target bio-electric tissue based on the measured values of $V_M$ and $V_M'$.

5. The method of claim 4, wherein the predetermined input impedance $R_1$ is much larger than the second predetermined input impedance $R_N$, and the parameter responsive to the impedance $R_D$ of the cardiovascular tissue between the sensing electrode and the target bio-electric tissue is determined based on an equation:

$$R_D \approx \frac{R_N(V_M - V_M')}{V_M'}.$$

6. The method of claim 4, wherein the response voltages $V_M$ and $V_M'$ are repeatedly measured, and the calculation of the parameter responsive to the impedance $R_D$ is repeatedly updated based on updated measurements of $V_M$ and $V_M'$.

7. The method of claim 6, wherein the calculated values of the parameter responsive to the impedance $R_D$ are displayed on a display.

8. The method of claim 7, wherein the method is carried out under processor control.

9. An apparatus, for use with an ECG monitor, the apparatus comprising:
a sensing electrode configured to touch a normally electric cardiovascular tissue;
an interface unit connectable to the sensing electrode and a reference electrode, wherein the interface unit is also connectable to at least a pair of ECG monitor inputs, the interface unit being configured to couple the sensing electrode and the reference electrode to an ECG monitor inputs having a predetermined input impedance $R_I$ and to also impose a second predetermined input impedance $R_N$ between the sensing electrode and the reference electrode, and being configured to measure a response voltage $V_M'$ with the second predetermined input impedance $R_N$ coupled between the sensing electrode and the reference electrode and being configured to measure a response voltage $V_M$ with the second predetermined input impedance $R_N$ not coupled between the sensing electrode and the reference electrode, the response voltages $V_M'$ and $V_M$ being the voltages generated in response to the normally bio-electric cardiovascular tissue being touched by the sensing electrode; and a processor being configured to determine whether the normally bio-electric cardiovascular tissue is bio-electrically active or inactive, wherein determining is based on the measured values of $V_M$ and $V_M'$.

10. The apparatus of claim 9, wherein the interface unit includes at least one switch to controllably connect and disconnect the second predetermined input impedance $R_N$ between the sensing electrode and the reference electrode.

11. The apparatus of claim 10, wherein the at least one switch comprises a pushbutton switch.

12. The apparatus of claim 10, wherein the at least one switch comprises a plurality of switches to controllably independently connect and disconnect any of more than one predetermined impedances between the sensing electrode and the reference electrode.

13. The apparatus of claim 9, wherein the interface unit is permanently connected to the sensing electrode.

14. The apparatus of claim 9, wherein the interface unit is configured to alternately impose the second predetermined input impedance $R_N$ between the sensing electrode and the reference electrode and not impose the second predetermined input impedance $R_N$ between the sensing electrode and the reference electrode.

15. The apparatus of claim 14, wherein the interface unit is further configured to repeatedly calculate a parameter responsive to an impedance $R_D$ of the cardiovascular tissue between the sensing electrode and a target bio-electric tissue as determined based on an equation:

$$R_D \approx \frac{R_N(V_M - V_M')}{V_M'}.$$

16. The apparatus of claim 15, wherein the interface unit comprises the processor.

17. The apparatus of claim 15, further comprised of a display coupled to the processor to display the parameter responsive to the impedance $R_D$ of the cardiovascular tissue between the sensing electrode and the target bio-electric tissue.

* * * * *